Figure 1:
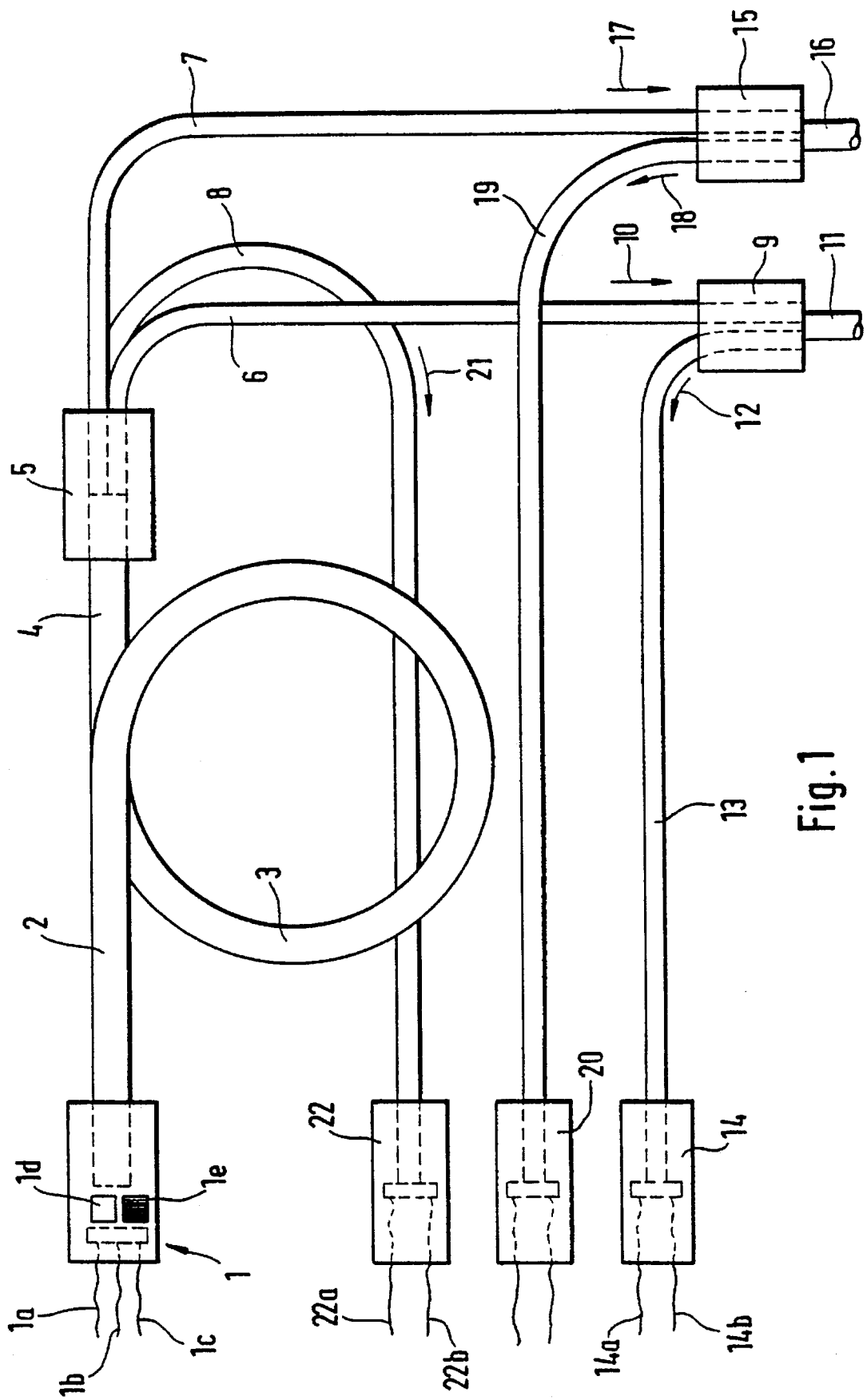

United States Patent [19]

Fischer et al.

[11] Patent Number: 5,522,389
[45] Date of Patent: Jun. 4, 1996

[54] SYSTEM FOR MEASURING A BLOOD PARAMETER AND METHOD THEREFOR

[75] Inventors: Bernhard Fischer, Leonberg; Peter Rother, Deckenpfronn, both of Germany

[73] Assignee: Hewlett-Packard Company, Palo Alto, Calif.

[21] Appl. No.: 724,865

[22] Filed: Jul. 2, 1991

[30] Foreign Application Priority Data

Sep. 28, 1990 [EP] European Pat. Off. ............ 90118662

[51] Int. Cl.⁶ .................................................... A61B 5/00
[52] U.S. Cl. ........................ 128/634; 356/41; 128/665
[58] Field of Search ...................... 128/633–4, 664–6; 356/41

[56] References Cited

U.S. PATENT DOCUMENTS

| | | | |
|---|---|---|---|
| 4,114,604 | 9/1978 | Shaw et al. | 128/634 |
| 4,178,917 | 12/1979 | Shapiro | 128/665 |
| 4,796,636 | 1/1989 | Branstetter et al. | 128/633 |
| 5,012,809 | 5/1991 | Shube | 128/634 |
| 5,047,627 | 9/1991 | Yim et al. | 128/634 |
| 5,066,859 | 11/1991 | Karkar et al. | 128/633 |
| 5,098,659 | 3/1992 | Yim et al. | 128/634 |
| 5,115,811 | 5/1992 | Hartkub et al. | 128/634 |
| 5,119,463 | 6/1992 | Vurek et al. | 128/634 |

Primary Examiner—Lee S. Cohen
Assistant Examiner—Robert L. Nassar, Jr.

[57] ABSTRACT

A system for measuring a blood parameter, such as pH, $pCO_2$ or $pO_2$, comprises an optical probe with an optical fiber and an invasive blood sensor. Light emitted by a light-emitting diode (1) is irradiated into an optical fiber (2). The system compensates for variations in the luminous efficiency of the LED (1) in that either a fraction of the light is fed directly to a photodetector (22), or in that the forward voltage of the LED is measured, and in that the signal received from the sensor is either normalized, or in that the LED drive current is adjusted accordingly.

5 Claims, 2 Drawing Sheets

SYSTEM FOR MEASURING A BLOOD PARAMETER AND METHOD THEREFOR

The present invention relates to a system for measuring a blood parameter such as pH, $pCO_2$ or $pO_2$ with an optical probe comprising at least an optical fiber connected with a monitor and an invasive blood sensor, wherein said monitor contains at least a light-emitting diode irradiating light into said optical fiber and a photoelement measuring the intensity of light fed back from said invasive blood sensor, and wherein said invasive blood sensor comprises a dye, preferably immobilized in a polymer, modifying the optical characteristics of the light irradiated by said light-emitting diode and means—preferably, a reflector—, for feeding back the modified light to said monitor.

Optical probes for the invasive measurement of blood parameters usually consist of at least one sensor which is connected with an associated monitor via an optical fiber. Typically, such probes comprise between one and three sensors, e.g. intended for the measurement of blood gases such as partial oxygen pressure ($pO_2$) or partial carbon dioxide pressure ($pCO_2$), or for the measurement of the pH value of the blood.

The monitor contains a light source which irradiates light into the optical fiber, the light thus being fed to the associated sensor. The sensor, in turn, comprises a polymer containing a dye (instead, the dye can also be immobilized in the optical fiber itself). The optical density or another optical parameter of said dye varies with the blood parameter to be measured. The light is then fed back via the same or another optical fiber to the monitor which contains a detector to measure light attenuation or changes in other optical parameters caused by the dye. This attenuation or change is a function of the blood parameter to be measured, and the relation between attenuation, absorbance or the change of another optical parameter and the blood parameter is well-known.

Usually, a reflector is positioned adjacent to the dye-containing polymer, opposite to the optical fiber. In such a sensor, light transmitted through the optical fiber passes the polymer, is reflected at the reflector, passes the polymer again and is then transmitted back. In this environment, only one optical fiber is required for each sensor. Further, as the light passes the dye-containing polymer twice, it is easier to detect any change in the optical characteristics of that dye. However, there are also other solutions like directing the light to a second optical fiber (when it has passed the polymer) and feeding said second optical fiber back to the monitor. The key point in all of these cases is that the light has to pass the polymer/dye zone where its optical characteristics is altered.

It has to be pointed out that an optical probe as described herein usually comprises three or even more sensors in order to measure various blood parameters with one probe. In these cases, the single optical fibers associated with the respective sensors are combined in a single cable for connection with the associated monitor. However, it is also possible to build an optical probe with one or two sensors only.

An optical probe as described herein can be introduced into a patient's artery to measure—depending on the dye—various blood parameters such a pH, $pO_2$ or $pCO_2$, as described above. It is also possible to integrate further components such as a strain relieving wire, an arterial pressure sensor, a temperature sensor or the like into the probe.

For a more detailed description of invasive fiber optic blood parameter measurement, reference is made to "Optical Fluorescence and its Application to an Intravascular Blood Gas Monitoring System", IEEE Transactions on Biomedical Engineering, Vol. BME-33, No. 2, February 1986, pages 117 ff., and "A Miniature Fiber Optic pH Sensor for Physiological Use", Journal of Biomedical Engineering, May 1980, pages 141 ff. For the details of the mechanical construction of optical probes as described herein, reference is further made to European patent applications EP-A-279004, EP-A-336984, EP-A-336985, European patent application number 90107850.1 and application number 90115496.3, which are incorporated in the disclosure of this description by reference.

The present invention deals with the light source providing light beams to the optical fibers and incorporated in the monitor. In former design proposals, high-output lamps have been used therefor. For example, Gehrich et al (Optical Fluorescence and its Application to an Intravascular Blood Gas Monitoring System, IEEE Transactions on Biomedical Engineering, Vol. BME-33, No. 2, February 1986, page 117, 123) propose to use a xenon arc source lamp. Goldstein et al (A Miniature Fiber Optic pH Sensor for Physiological Use, Journal of Biomedical Engineering, May 1980, page 141, 143) use a halogen 150-watt projector lamp for the same purpose. As these light sources provide white or approximately white light, filters have to be used to feed light of a limited pass-band into the optical fiber. Both Gehrich et al and Goldstein et al use a filter wheel to generate light of different colors (the light-emitting diodes in the Goldstein et al design are only used to detect the position of the filter wheel).

Using xenon or halogen lamps (one could also use krypton lamps or tungsten lamps as well) has the advantage that light of high intensity is generated, so that the sensor is always sufficiently supplied with light, even in the case of considerable transmission losses. However, the optical system consisting of a high-output lamp, a filter wheel and the associated mechanical drive as well as condensing lenses is bulky, difficult to manufacture and increases the price of the product. Further, such lamps have only a limited lifetime, and the associated mechanics may fail, so that the system is quite error-prone.

In case of the present invention, the inventors have therefore decided to use light-emitting diodes as light sources for the optical system. Light-emitting diodes (LEDs) of sufficient light output are already available on the market, and they yield satisfying results in an optical system as described herein, in particular if the whole system is designed to avoid transmission losses. Using LEDs has particularly the advantage of low manufacturing and component costs and long lifetime.

The accuracy of the measurement with a system of the kind described herein depends on the stability of the light source, i.e. an important design criterion is that the intensity of the light fed to the sensors is constant.

One factor influencing the intensity of light provided to the sensors is the amount of environmental light, which also contains components of the wavelength used for actual measurement. Compensation of such environmental light can be obtained—as it is known in the art—by strobing (intermittently actuating) the light source, measuring the intensity of the environmental light in the phases where the light source is switched off and subtracting the environmental component from the measured intensity, or otherwise correcting the measured value in dependence of the environmental light intensity.

A further reason for measurement inaccuracy may be sensor or probe artefacts, e.g. caused by movement or bending of the optical fiber. As will be explained in more detail below, such artifacts can be compensated in that two wavelengths are used, e.g. red and green.

The above measures which compensate for factors influencing the accuracy of the measurement are largely sufficient in systems using a high-output lamp as a light source. However, in case of light-emitting diodes, the inventors have noted that the accuracy of the measurement and the blood parameter readings are not always satisfying. In particular, tests have shown that the readings obtained with LEDs as light sources are subject to various drift effects.

It is a major objective of the present invention to improve the above described system such that the drift effects are compensated, and that measurement accuracy is improved.

Further investigations revealed that the above drift effects which have considerable influence on the readings of the monitor have primarily two reasons: The first is that the intensity of the emitted light varies with the LED temperature, and the second is a degradation which depends on the operating time of each LED. It has turned out that these effects have unexpectedly considerable influence on the accuracy of the system. The difficulty in detecting the reason for the incorrect reading of the system in the present case was that such effects were not known from the light sources used in the prior art, namely xenon and halogen lamps. In fact, the above described effects influence the reading of a system equipped with a high intensity lamp not or only marginally.

In order to minimize or avoid faulty readings, the present invention proposes to provide, in a system as described above, means for feeding a fraction of the light emitted by said light-emitting diode directly to a photodetector measuring the luminous efficiency of said fraction of light and converting it into an electrical signal, and further to provide means for correcting the intensity of the light fed back from said invasive blood sensor in dependence of the electrical signal generated by said photodetector.

According to the invention, the intensity of the LED or the LEDs is directly measured in that a part or fraction of the light is not fed to the invasive blood sensor, but directly to a photodetector instead. "Directly" in the context used here means that the light is not fed via any blood gas sensor to a photodetector; preferably, the direct connection is performed inside the monitor. The photodetector converts the intensity of the received light into an electrical signal which is representative of the intensity of the light emitted by the LED. This electrical signal represents all variations in the LED luminous efficiency (intensity) caused by temperature effects or by degradation. It is therefore fed to correction means which may now correct the signal received from the invasive blood sensor accordingly, thus compensating for any variations in the intensity of the transmitter LED. Therefore, the reading of the system becomes highly accurate and reliable.

In a preferred embodiment, the light emitted by the LED is fed to a beam splitter, preferably via an optical fiber, wherein said beam splitter splits the light emitted by the light-emitting diode into at least a first beam fed to the optical fiber (and, therefore, to the invasive blood sensor) and at least a second beam feeding said fraction of light to the photodetector. The beam splitter ensures that the photodetector always receives a constant fraction of the emitted light. Further, it makes splitting of the light easier; as is basically known in the art, light-emitting diodes have only a very small active surface, and therefore it would be disadvantageous to use several optical fibers with their ends arranged adjacent to the active luminous area of the LED. Further, connecting the beam splitter with the transmitter LED via an optical fiber has the advantage that the light is mixed in the optical fiber so that the luminous density is constant over the whole cross-section of the fiber at the end adjoining the beam splitter. Preferably, the connection between the beam splitter and the photodetector comprises also an optical fiber.

According to another aspect of the present invention, means are provided for measuring a physical property representative of the luminous efficiency of the light-emitting diode and for converting the measurement value of said physical property into an electrical signal, and further means are used for correcting the intensity of the light fed back from the invasive blood sensor in dependence of the electrical signal generated by said physical property measuring means. According to this aspect of the invention, the intensity or luminous efficiency of the light-emitting diode is not measured directly, but via another physical parameter instead. Such solution may be advantageous in order to reduce the necessary components and therefore the price of the product. In particular, a physical property related to and indicative of the luminous efficiency is the temperature of the light-emitting diode. If temperature measuring means are used to determine the temperature of the LED, the intensity of the light fed back from the invasive blood sensor may be corrected accordingly.

As the temperature is related to the luminous efficiency of an LED, this is an easy-to-implement solution for cancelling out temperature effects, whether caused by the environmental temperature or the temperature increase caused by the operation of the LED. As temperature effects are the most significant effects reducing the accuracy of the measurement, it is sufficient for a lot of applications, although it does not consider the degradation of the LED.

In an advantageous embodiment, the temperature is measured indirectly in that the forward voltage of the LED is measured instead. There is a direct relation between the forward voltage and the absolute temperature of the LED; the characteristic curve of a diode operated in the forward direction is $$I = I_0(e^{U/U_T} - 1) \tag{1}$$

wherein I is the LED current, $I_0$ is the maximum current if operated in reverse direction, U is the forward voltage and $U_T$ is the temperature voltage, which is defined as follows:

$$U_T = \frac{kT}{e_0} \tag{2}$$

k being the Boltzmann constant, T the absolute temperature and $e_0$ the elemental charge.

If we substitute equation (2) into equation (1) and solve it with respect to T, we obtain $$T = \frac{Ue_0}{k} \cdot \frac{1}{\ln(1 + I/I_0)} \tag{3}$$

By this, the forward voltage is directly related to the temperature and therefore to the luminous efficiency of the LED. This solution is very inexpensive and easy to implement as components for measuring a voltage, whether digital or analog, are common elements in electronics.

In an advantageous embodiment of the present invention, said means for correcting the intensity of the light fed back from the invasive blood sensor comprises normalizing means. Such normalizing means normalize the intensity of the light fed back from the invasive blood sensor with respect to the electrical signal generated by said photodetector or by said physical property measuring means, in particular by the equation $$I_{normalized} = \frac{I_{measured}}{I_{reference}} \quad (4)$$

wherein $I_{normalized}$ is the normalized intensity, $I_{measured}$ is the intensity of the light fed back to the monitor, and $I_{reference}$ is the intensity measured by the photodetector or the physical property measuring means. This is an easy way to implement correction means, particularly if a microprocessor—which is anyway comprised in most state of the art monitors—is used to perform the necessary calculations. In particular, this solution requires no additional hardware and does therefore not increase the production costs. However, it is understood that not only microprocessor could be used as normalizing means, but that other digital circuitry or standard analog electronics could be used as well.

As already outlined above, sensor artefacts can be eliminated in that the system is operated with two different wavelengths, e.g. green and red light, wherein the light of one wavelength is modified by the dye-containing polymer in the invasive blood sensor and the light of the other wavelength is basically not. Changes in the wavelength not influenced by the polymer indicate e.g. movement or bending of the optical fiber and can therefore be used to correct the reading accordingly. (Usually, red light is used for reference measurements). It is advantageous to combine this solution with the present invention as all relevant sources of error can be eliminated in this way, in particular if the intensity of the environmental light is also taken into consideration. In this case, two light emitting diodes (e.g. a green and a red LED), or a dual light emitting diode, are used. In combination with the present invention, light of both wavelengths is also fed directly to a photodetector, or the temperature/forward voltage of both LEDs is measured.

Although it is possible to operate both LEDs at the same time and to use photoelements which are only sensitive to light of a certain wavelength, it is easier and therefore preferred to operate said two diodes alternately. That is, the LEDs are strobed, so that, at a certain point in time, only light of one wavelength is emitted. This reduces the need for a photoelement with selective characteristics.

If normalization is done in a system with more than one wavelength, the normalized intensity is preferably calculated by means of the following equation:

$$I_{normalized} = \frac{\frac{I_{\lambda 1, measured}}{I_{\lambda 2, measured}}}{\frac{I_{\lambda 1, reference}}{I_{\lambda 2, reference}}}, \quad (5)$$

wherein $I_{\lambda 1, measured}$ is the intensity of the light of the first wavelength fed back to the monitor from the invasive blood gas sensor. $I_{\lambda 2, measured}$ is the intensity of the light of the second wavelength fed back to the monitor, $I_{\lambda 1, reference}$ is the intensity at the first wavelength measured by the photodetector or the physical property measuring means, and $I_{\lambda 2, reference}$ is the intensity at the second wavelength measured by the photodetector or the physical property measuring means. Using normalizing means implementing the above equation has the advantage that two effects influencing measurement accuracy can be compensated in a single corrective step. In the above equation, it is assumed that $I_{\lambda 1, measured}$ and $I_{\lambda 2, measured}$ are already corrected for the environmental (background) component of the light. Such correction of the background component is not required for the reference intensities, as they are shielded from ambient light inside the monitor.

According to a further advantageous, alternative embodiment, the electrical signal generated by the photodetector or by the physical property measuring means is used to actuate means for controlling the drive current of the light-emitting diode(s) in dependence of the electrical signal. In this solution, no. corrective action on the signal received from the invasive blood sensor has to be taken, i.e. this signal needs not to be modified; instead, the drive current of the LED is varied accordingly, in order to compensate for any deviations, e.g. by means of a controlled current source. This is also an inexpensive and easy-to-implement solution; however, care has to be taken that no "thermal run-away" occurs (this happens if the LED is operated with a current that causes self-heating of the LED, which in turn causes a reduction of luminous efficiency, which in turn causes the control circuit to increase the LED drive current, so that the LED is finally destroyed). It may therefore be advantageous to use a current limiting circuit for the LED drive current in this environment.

The invention further relates to a method for measuring a blood parameter such as pH, $pCO_2$ or $pO_2$, comprising the steps of feeding light originating from a light-emitting diode via an optical fiber to an invasive blood sensor, directing the light through a dye-containing polymer which modifies the optical characteristics of said light, and feeding said modified light back to a detector (photoelement). According to the method proposed herein, a physical property representative of the luminous efficiency of the light-emitting diode is measured (in particular by feeding a fraction of the light directly to a photodetector or by measuring the temperature and/or the forward voltage of the light-emitting diode), and the measurement value of said physical property is converted into an electrical signal. According to a first method, the intensity of the light fed back from the invasive blood sensor is then corrected in dependence of the electrical signal. According to another embodiment, the drive current of the light-emitting diode is controlled in dependence of the electrical signal.

Figure 2:
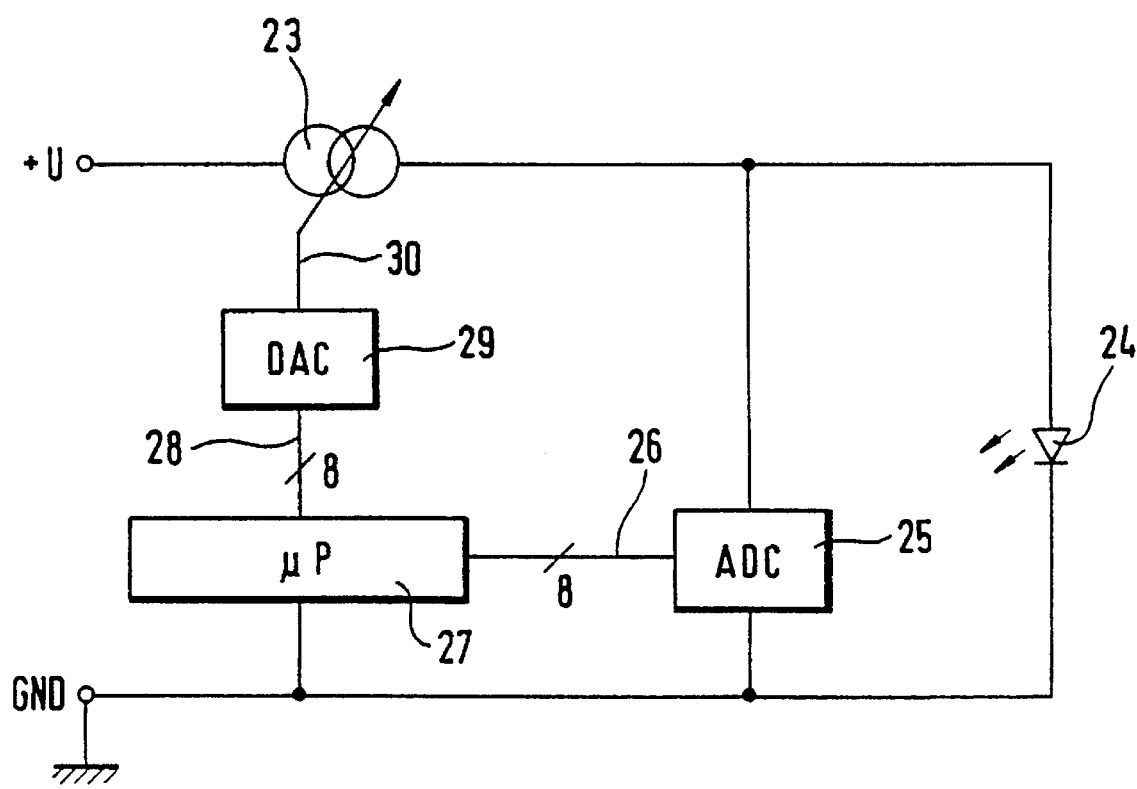

The invention will now be explained, by means of a non-limiting example, with reference to the enclosed drawings, in which FIG. 1 depicts a first embodiment of the invention, wherein a fraction of the emitted light is fed directly to a photodetector, and FIG. 2 shows the block diagram of a second embodiment, wherein the forward voltage of the LED is recorded.

FIG. 1 depicts a system for measuring blood parameters, insofar as it is contained in the monitor. A light-emitting diode 1 is used to irradiate light into an optical fiber 2. LED 1 is a dual LED which is able to emit green or red light, dependent on the control signals applied to their connection wires 1a, 1b or 1c. LED 1 comprises a first p/n junction 1d (emitting green light) and a second p/n junction 1e (emitting red light) for this purpose.

Optical fiber 2 has a diameter of 1 millimeter (mm). It has a length—as indicated by the circle-like configuration 3—sufficient to obtain a uniform distribution of the light over the whole cross-section of the optical fiber. That is, at the end 4 of this optical fiber, distribution of the light is uniform (constant density), regardless whether green or red light is irradiated into the fiber.

Optical fiber 2, 3, 4 is connected with a beam splitter 5. This beam splitter splits the light into three beams, whereby—due to the uniform distribution of the light— the relation of the transmitted intensities of light among the various connections is always constant in relation to each other.

Beam splitter 5 is connected with three optical fibers 6, 7 and 8. Optical fiber 6 is connected with an optical light transmission element 9; the direction of the light is indicated by arrow 10.

Element 9 is further connected with an optical fiber 11 which, in turn, is in connection with a pH sensor (not shown). In the pH sensor, the light passes a dye-containing polymer and is then reflected back into optical fiber 11. It passes element 9 again in the direction of arrow 12 and is fed via optical fiber 13 to a photoelement 14 generating an electrical signal (e.g. a voltage signal) indicative of the received intensity. The electrical signal is fed to a microprocessor (not shown) via wires 14a and 14b. An example for optical transmission element 9 is e.g. described in German patent application DE-OS 36 08 465, which is hereby incorporated into the disclosure of the present description by reference.

In similar manner, optical fiber 7 is connected with a second optical transmission element 15, which, in turn, is connected—via optical fiber 16—with a $pCO_2$ sensor of basically similar construction as the pH sensor. The direction of the light is again indicated by arrows 17 and 18. Optical fiber 19 feeds the light received from the $pCO_2$ sensor to a second photoelement 20 which is of similar construction as photoelement 14 (e.g., a photodiode or a phototransistor).

Optical fiber 8 feeds light from beam splitter 5 directly—in the direction of arrow 21—to a photodetector 22, also of similar construction as photoelements 14 and 20. Photodetector 22 converts the intensity of the received light into a proportional electrical signal which is fed via wires 22a and 22b—via an analog-to-digital converter—to a microprocessor (both not shown).

In operation, green and red light generated by LED 1 is fed alternately into optical fiber 2. There are also time intervals where neither green nor red light is fed into the fiber, so that photoelements 14 and 20 receive and measure environmental light, in order to take appropriate corrective action. Light of the green wavelength is modified by the polymer contained in the sensors according to the blood parameter to be measured (i.e. pH or $pCO_2$). Red light is not modified by said polymer. The reflected light of both wavelengths is then recorded by photoelements 14 and 20. As variations in the intensity of the red light indicate sensor artefacts, compensation is also possible.

A constant fraction of the light—this applies to the red as well as to the green light—is further fed via optical fiber 8 to photodetector 22. The signal generated by this photodetector represents changes in the intensity or luminous efficiency of the LED e.g. caused by temperature effects or by degradation (of course, it records also changes in the intensity caused by other effects).

In order to compensate for sensor artefacts as well as for variations in the LED intensity, the received signals are normalized according to the following equation:

$$I_{normalized} = \frac{\frac{I_{red,measured}}{I_{green,measured}}}{\frac{I_{red,reference}}{I_{green,reference}}} \quad (6)$$

wherein $I_{red,measured}$ is the signal recorded by photoelement 14 or photoelement 20 when the source emits red light, $I_{green,measured}$ is the signal recorded by these photoelements when the source emits green light, $I_{red,reference}$ is the signal recorded by photodetector 22 when the source emits red light and—similarly—$I_{green,reference}$ is the signal recorded by photodetector 22 when the source emits green light.

Although the environment depicted in FIG. 1 is able to feed light to two invasive blood sensors, namely a pH sensor and a $pCO_2$ sensor, it is understood that this is not a necessary design; instead, it could also comprise one sensor only (in which case optical fibers 7, 16 and 19, element 15 and photoelement 20 would be superfluous), or more than 2 sensors. Further, although the present invention is primarily intended for use with absorbance-type sensors such as pH or $pCO_2$, it could also be used with a sensor of the fluorescent type, like a $pO_2$ sensor. All of the components shown in FIG. 1 are usually components contained in the monitor.

A second embodiment is shown in simplified manner in FIG. 2. A controllable current source 23 provides a current to LED 24. The forward voltage of LED 24 is recorded by an analog-to-digital converter 25, which, in turn, feeds the digitized signal via connection 26 to microprocessor 27. The microprocessor performs the necessary calculations to compensate for any variations in the LED intensity (which are related to the temperature and, therefore, to the forward voltage of LED 24) and feeds a digital control signal—via line 28—to digital-to-analog converter 29. This digital-to-analog converter controls, in turn, current source 23 via line 30.

It is understood that the circuit diagram shown in FIG. 2 is simplified insofar as, in a monitor, two LEDs (red and green) would be needed, wherein the second LED is connected to the rest of the circuitry in similar manner. Both LEDs could also be connected with the same analog-to-digital converter via a multiplexer. It is further understood that the digital circuitry, i.e. components 25, 27 and 29, are not mandatory. Instead, an analog circuitry could also be selected.

In operation, the current generated by current source 23 is fed to LED 24. If the temperature (and, therefore, the luminous efficiency) of LED 24 varies, ADC 25 records a change in the forward voltage of this LED. Microprocessor 27 then increases the excitation current (via DAC 29 and controllable current source 23) accordingly, so that the intensity of LED 24 is kept constant. Although the circuit in FIG. 2 does not depict a current limiting circuit, such could be useful in order to avoid destruction of LED 24 by excessive excitation current.

The circuits shown in FIG. 1 and 2 depict two methods for measuring the variation of the luminous efficiency of the LED, namely measuring the intensity of a fraction of the emitted light and measuring the forward voltage of the LED. Further, two ways are shown to compensate for a change in intensity, namely to normalize the measurement signal, or to keep the intensity constant by controlling the LED excitation current. It is understood that these methods and the components necessary to perform them could also be combined in a manner different than shown in the previous examples, for example by measuring a fraction of the emitted light and controlling the LED drive current accordingly, or to measure the LED forward voltage and to normalize the received signal accordingly.

We claim:

1. A system for measuring a blood parameter such as pH, $pCO_2$ or $pO_2$, said system comprising:

an optical probe including a blood sensor and a connected probe optical fiber, said blood sensor including a dye that modifies optical characteristics of light fed from said probe optical fiber, and reflective means for feeding back modified light into said probe optical fiber;

monitor means including light-emitting diode means for radiating a light beam, a first photo detector and a second photo detector;

an excitation optical fiber coupled to said light emitting diode means and terminating in a beam splitting means, said excitation optical fiber having a sufficient length that enables, at said beam splitting means, a uniform distribution thereacross of light emitted from said light emitting diode means, said beam splitting means thereby providing a plurality of split light beams with intensities that are constant with respect to each other;

light fiber means coupling a first said split light beam to said first photodetector and a second said split beam to a coupler that is connected to said probe optical fiber, said light fiber means also coupling light fed back from said blood sensor through said coupler to said second photodetector;

whereby said first photodetector provides a correction signal indicative of said first split light beam's intensity and said second photodetector provides a sense signal indicative of said fed back light's intensity, said monitor means employing said correction signal to correct said sense signal so as to achieve an accurate measurement of said blood parameter.

2. A system according to claim 1, wherein said monitor means further comprises: means for normalizing a value derived from said sense signal that is indicative of the intensity of the light fed back from said blood sensor with respect to a value derived from the correction signal, said means employing the equation $$I_{normalized} = \frac{I_{measured}}{I_{reference}}$$

wherein $I_{normalized}$ is the normalized intensity, $I_{measured}$ is the intensity of the light fed back to said second photodetector, and $I_{reference}$ is the light intensity measured by said first photodetector.

3. A system according to claim 1, wherein said light emitting diode means comprises at least two light-emitting diodes, or a dual-light emitting diode for emitting light of different wavelengths wherein the light of the first wavelength is modified by the dye in the blood sensor and the light of the second wavelength is substantially not modified thereby.

4. A system according to claim 3, wherein said at least two light-emitting diodes or said dual-light emitting diode are actuated alternately.

5. A system according to claim 3, wherein the light fed back from said optical probe is normalized, said monitor means calculating a normalized intensity by means of the following equation:

$$I_{normalized} = \frac{\frac{I_{\lambda 1, measured}}{I_{\lambda 2, measured}}}{\frac{I_{\lambda 1, reference}}{I_{\lambda 2, reference}}}$$

wherein $I_{\lambda 1, measured}$ is the intensity of light of the first wavelength fed back to said second photodetector, $I_{\lambda 2, measured}$ is the intensity of the light of the second wavelength fed back to said second photodetector, $I_{\lambda 1, reference}$ is the intensity of light of the first wavelength measured by said first photodetector, and $I_{\lambda 2, reference}$ is the intensity of light of the second wavelength measured by said first photodetector.

* * * * *